US012724026B2

(12) United States Patent
Ng

(10) Patent No.: US 12,724,026 B2
(45) Date of Patent: Sep. 1, 2026

(54) LOCALIZED SURFACE PLASMON RESONANCE BIOSENSING DEVICE

(71) Applicant: Rafael Biotechnology Company Limited, Hong Kong (CN)

(72) Inventor: Siu Pang Ng, Hong Kong (CN)

(73) Assignee: Rafael Biotechnology Company Limited, Hong Kong (CN)

( * ) Notice: Subject to any disclaimer, the term of this patent is extended or adjusted under 35 U.S.C. 154(b) by 690 days.

(21) Appl. No.: 17/931,743

(22) Filed: Sep. 13, 2022

(65) Prior Publication Data

US 2024/0036038 A1 Feb. 1, 2024

(30) Foreign Application Priority Data

Jul. 28, 2022 (CN) ........................ 202210899851.9

(51) Int. Cl.
*G01N 33/543* (2006.01)
*G01N 21/552* (2014.01)

(52) U.S. Cl.
CPC ..... *G01N 33/54373* (2013.01); *G01N 21/553* (2013.01)

(58) Field of Classification Search
None
See application file for complete search history.

(56) References Cited

U.S. PATENT DOCUMENTS 8,958,999 B1 2/2015 Ptasinski et al.
2002/0054290 A1* 5/2002 Vurens ..................... G01J 4/04 356/369
2003/0103208 A1 6/2003 Quinn et al.
2005/0018949 A1 1/2005 Yan
2007/0109542 A1* 5/2007 Tracy .................. G01N 21/553 356/445
2008/0278728 A1 11/2008 Tetz et al.
2009/0117669 A1* 5/2009 Yamamichi .......... G01N 21/554 436/525
2009/0213382 A1 8/2009 Tracy et al.
2010/0078575 A1 4/2010 Reilly et al.
2014/0093977 A1 4/2014 Raphael et al.
2014/0354979 A1 12/2014 Li et al.
2016/0178516 A1 6/2016 Abdulhalim (Continued)

FOREIGN PATENT DOCUMENTS

CN 1588064 A * 3/2005 ............ G01N 21/45
CN 1724969 A 1/2006
CN 1731180 A 2/2006

(Continued)

*Primary Examiner* — Matthew D Krcha
(74) *Attorney, Agent, or Firm* — The Webb Law Firm

(57) ABSTRACT

A localized surface plasmon resonance biosensing device is disclosed, including a laser source; a first linear polarizer configured for linearly polarizing probe laser; a plasmonic microarray biochip configured for receiving the linearly polarized probe laser; a photothermal excitation assembly configured for outputting an optical wave acted on an optical waveguide array of the plasmonic microarray biochip; an optical interference assembly configured for converting laser transmitted by the plasmonic microarray biochip into double beams meeting an interference condition; a telecentric lens; and an imaging chip configured for acquiring a laser speckle image formed by interference of the double beams.

7 Claims, 8 Drawing Sheets

(56) References Cited

U.S. PATENT DOCUMENTS

| | | | | |
|---|---|---|---|---|
| 2018/0017917 | A1 | 1/2018 | Takahashi et al. | |
| 2020/0150028 | A1* | 5/2020 | Ünlü | G01N 21/21 |

FOREIGN PATENT DOCUMENTS

| | | | | | |
|---|---|---|---|---|---|
| CN | 106896095 | A | | 6/2017 | |
| CN | 107764747 | A | | 3/2018 | |
| CN | 109211934 | A | * | 1/2019 | G01N 21/952 |
| CN | 112033932 | A | * | 12/2020 | G01N 21/41 |
| CN | 112858223 | A | | 5/2021 | |
| KR | 20110100007 | A | | 9/2011 | |
| WO | 2005022131 | A1 | | 3/2005 | |
| WO | WO-2016201189 | A1 | * | 12/2016 | G01N 21/553 |
| WO | WO-2021204479 | A1 | * | 10/2021 | C12Q 1/6816 |
| WO | 2022047847 | A1 | | 3/2022 | |

* cited by examiner

LOCALIZED SURFACE PLASMON RESONANCE BIOSENSING DEVICE

CROSS-REFERENCE TO RELATED APPLICATION

This application is claims priority to Chinese Patent Application No. 202210899851.9 filed Jul. 28, 2022, the disclosure of which is hereby incorporated by reference in its entirety.

BACKGROUND

Technical Field

The disclosure relates to the technical field of biosensing, and particularly to a localized surface plasmon resonance biosensing device.

Technical Description

Surface plasmon resonance imaging (SPRi) is an established label-free biosensing technique with accepted performance and accuracy. Existing SPRi biosensors are usually designed and fabricated with the Kretschmann configuration composed of a thin metallic gold film coated glass prism. There are two major problems found after use: (1) there is a limited accuracy in the measurement method, wherein on one hand, the sensitivity of the SPRi biosensor is not at an angle where resonance occurs when the light intensity change is measured, which reduces the sensitivity, and on the other hand, accuracy limitation on measurement of rotating angle is involved when the angle change is measured, and the signal is weakened due to the extinction effect caused by resonance when the laser phase is measured; and (2) the imaging effect is not satisfactory, wherein a total reflection light path is generally used in the existing SPR imaging system, in which the incident angle and the reflected angle are both very large, but the camera and the optical lens generally adopt plane imaging, which has a limited depth of field of imaging, so that the SPR imaging biosensor has at most 32 channels, leading to a limited number of biosensing channels.

SUMMARY

The disclosure aims at solving at least one of the technical problems in the existing technology. Therefore, the disclosure proposes a localized surface plasmon resonance biosensing device, which can improve the measurement accuracy and the imaging effect.

A localized surface plasmon resonance biosensing device according to an embodiment of the disclosure comprises a laser source configured for outputting a probe laser; a first linear polarizer arranged in front of the laser source and configured for linearly polarizing the probe laser; a plasmonic microarray biochip arranged in front of the first linear polarizer to receive the linearly polarized probe laser, wherein the plasmonic microarray biochip comprises a transparent substrate, and an optical waveguide array and a microfluidic channel which are arranged at a middle portion of the transparent substrate, and an optical waveguide side surface of the optical waveguide array is provided with titanium nitride nanocubes; a photothermal excitation assembly configured for outputting an optical wave acted on the optical waveguide array of the plasmonic microarray biochip; an optical interference assembly arranged in front of the plasmonic microarray biochip and configured for converting laser transmitted by the plasmonic microarray biochip into double beams meeting an interference condition; a telecentric lens arranged on an output side of the optical interference assembly and configured for focusing the double beams; and an imaging chip arranged at a tail portion of the telecentric lens and configured for acquiring a laser speckle image formed by interference of the double beams.

The localized surface plasmon resonance biosensing device according to an embodiment of the disclosure at least has the following beneficial effects.

By using laser as an excitation source which acts on the titanium nitride nanocubes on the plasmonic microarray biochip, surface enhanced elastic scattering is produced during localized surface plasmon resonance, and the LSPR phase is amplified. Meanwhile, the localized temperature in vicinity of the titanium nitride nanocubes is increased through the photothermal excitation assembly, the specificity of target-receptor interaction is enhanced. The laser speckle image subjected to double enhancements is acquired by the optical interference assembly, the telecentric lens and the imaging chip, and a more accurate phase is analyzed by using the sensitivity of a laser speckle to a localized refractive index change.

According to some embodiments of the disclosure, a collimating unit is arranged between the laser source and the first linear polarizer.

According to some embodiments of the disclosure, the collimating unit is a plano-convex lens, an output end of the laser source is connected with a single mode fiber, and an exit of the single mode fiber is located at a focus of the plano-convex lens.

According to some embodiments of the disclosure, the laser source is a 640-nm single mode laser diode, a shell of the 640-nm single mode laser diode is connected with a first temperature sensor and a first thermoelectric cooler, and the first temperature sensor and the first thermoelectric cooler are electrically connected with a first temperature controller respectively.

According to some embodiments of the disclosure, the photothermal excitation assembly is a light emitting diode.

According to some embodiments of the disclosure, the optical interference assembly comprises a light splitting prism, a first reflector and a second reflector, a light incident surface of the light splitting prism faces the plasmonic microarray biochip, and the first reflector and the second reflector are respectively located at a first interference port and a second interference port of the light splitting prism.

According to some embodiments of the disclosure, the first reflector is arranged on a kinetic mount configured for manually and finely adjusting a distance, and the second reflector is arranged on a piezoelectric ceramic phase shifter.

According to some embodiments of the disclosure, a second linear polarizer is arranged between the optical interference assembly and the telecentric lens, and the second linear polarizer has a polarization direction rotated by 90 degrees relative to a polarization direction of the first linear polarizer.

According to some embodiments of the disclosure, a narrow-pass laser filter is arranged between the telecentric lens and the second linear polarizer.

According to some embodiments of the disclosure, a shell of the imaging chip is connected with a second temperature sensor and a second thermoelectric cooler, and the second temperature sensor and the second thermoelectric cooler are electrically connected with a second temperature controller respectively.

Additional aspects and advantages of the disclosure will be explained in part in the following description, which can become apparent from the following description or be understood through practice of the disclosure.

BRIEF DESCRIPTION OF THE DRAWINGS

The disclosure is further described hereinafter with reference to the drawings and the embodiments, wherein.

REFERENCE NUMERALS

Figure 1:
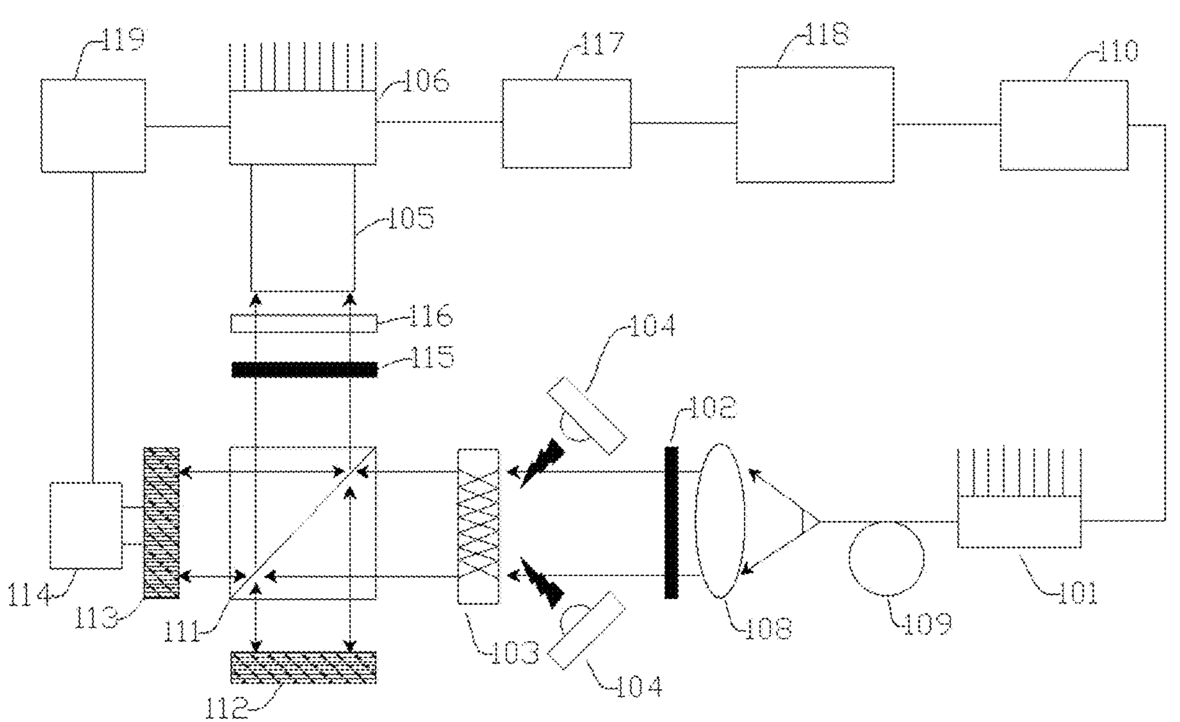
FIG. 1 is a schematic diagram of a localized surface plasmon resonance biosensing device according to an embodiment of the disclosure.

101 refers to laser source, 102 refers to first linear polarizer, 103 refers to plasmonic microarray biochip, 104 refers to photothermal excitation assembly, 105 refers to telecentric lens, 106 refers to imaging chip, 107 refers to matt-black anodized aluminum enclosure, 108 refers to collimating unit, 109 refers to single mode fiber, 110 refers to first temperature controller, 111 refers to light splitting prism, 112 refers to first reflector, 113 refers to second reflector, 114 refers to piezoelectric ceramic phase shifter, 115 refers to second linear polarizer, 116 refers to narrow-pass laser filter, 117 refers to second temperature controller, 118 refers to phase direct-current power supply, and 119 refers to MCU singlechip.

DETAILED DESCRIPTION

The embodiments of the disclosure will be described in detail hereinafter. Examples of the embodiments are shown in the drawings. The same or similar reference numerals throughout the drawings denote the same or similar elements or elements having the same or similar functions. The embodiments described below by reference to the drawings are exemplary and are intended only to explain the disclosure and are not to be construed as limiting the disclosure.

In the description of the disclosure, it should be understood that the orientation or position relation related to the orientation description, such as the orientation or position relation indicated by upper, lower, etc. is based on the orientation or position relation shown in the drawings, which is only configured for the convenience of description of the disclosure and simplification of description instead of indicating or implying that the indicated device or element must have a specific orientation, and be constructed and operated in a specific orientation, and thus should not be understood as a limitation to the disclosure.

In the description of the disclosure, multiple refers to being two or more. If there are the descriptions of first and second, it is only for the purpose of distinguishing between technical features, and should not be understood as indicating or implying relative importance, implicitly indicating the number of the indicated technical features or implicitly indicating the order of the indicated technical features.

In the description of the disclosure, words such as setup, installation, and connection should be understood in a broad sense unless otherwise expressly defined, and those having ordinary skills in the art may reasonably determine the specific meanings of the above words in the disclosure with reference to the context of the technical solution.

Figure 2:
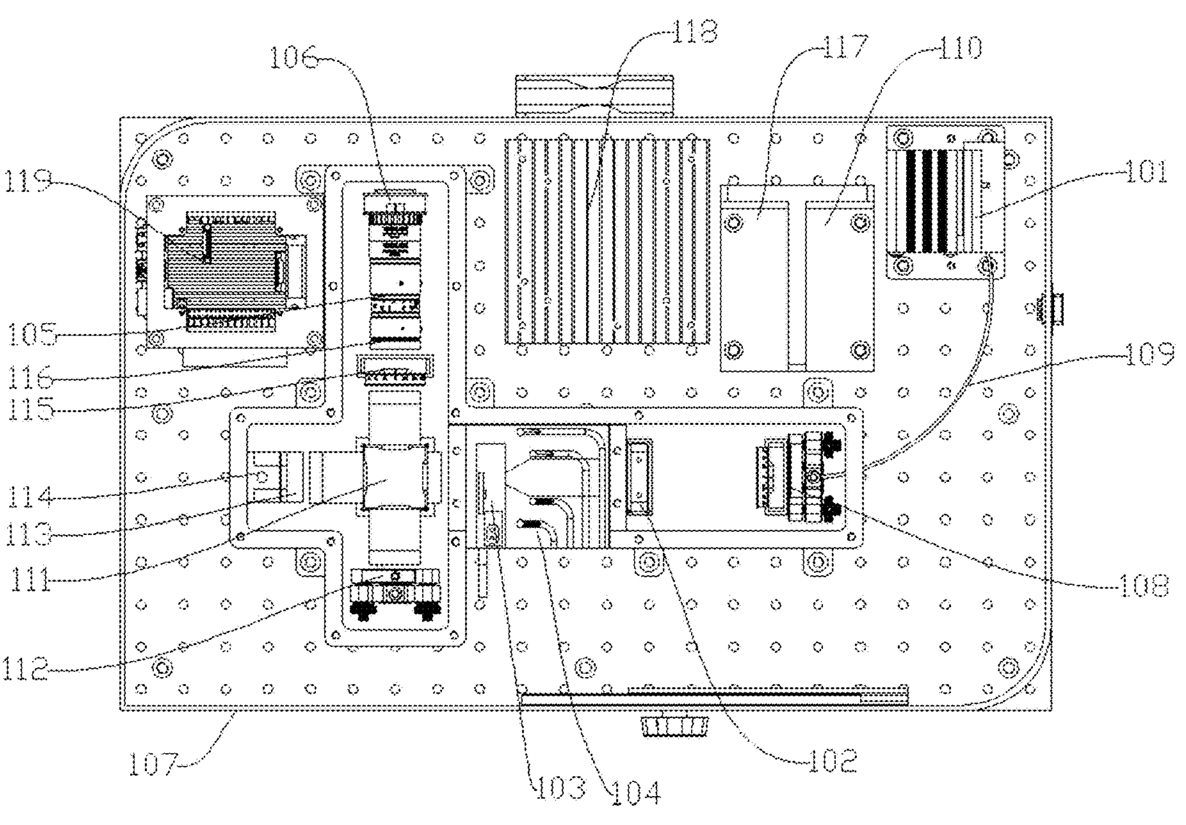
FIG. 2 is a schematic diagram of an internal structure of the localized surface plasmon resonance biosensing device according to an embodiment of the disclosure.

With reference to FIG. 1 and FIG. 2, a localized surface plasmon resonance biosensing device according to an embodiment of the disclosure comprises a laser source 101, a first linear polarizer 102, a plasmonic microarray biochip 103, a photothermal excitation assembly 104, an optical interference assembly, a telecentric lens 105, an imaging chip 106 and other main components.

The laser source 101 is configured for outputting a probe laser. The first linear polarizer 102 is arranged in front of the laser source 101 and configured for linearly polarizing the probe laser, which specifically refers to rotating by 45 degrees relative to an optical axis in this embodiment.

The plasmonic microarray biochip 103 is arranged in front of the first linear polarizer 102 to receive the linearly polarized probe laser, wherein the plasmonic microarray biochip 103 comprises a transparent substrate, and an optical waveguide array and a microfluidic channel which are arranged at a middle portion of the transparent substrate, and an optical waveguide side surface of the optical waveguide array is provided with titanium nitride nanocubes. A schematic diagram of a specific structure may refer to a localized surface plasmon resonance biochip 103 and a manufacturing method therefor, a biosensing system including same, and an application of the biosensing system disclosed in CN202010931465.4, it can be seen that by using the titanium nitride nanomaterial instead of the gold material, not only the resolution can be ensured, but also the material cost can be significantly reduced, and the titanium nitride can reduce the number of chemical substances involved and improve the detection accuracy.

The photothermal excitation assembly 104 is configured for outputting an optical wave acted on the optical waveguide array of the plasmonic microarray biochip 103, which can induce the thermoplasmonic effect and enhance the specificity of target-receptor interaction.

The optical interference assembly is arranged in front of the plasmonic microarray biochip 103 and configured for converting laser transmitted by the plasmonic microarray biochip 103 into double beams meeting an interference condition. The telecentric lens 105 is arranged on an output side of the optical interference assembly and configured for focusing the double beams. The imaging chip 106 is arranged at a tail portion of the telecentric lens 105 and configured for acquiring a laser speckle image formed by interference of the double beams.

In this embodiment, by using laser as an excitation source which acts on the titanium nitride nanocubes on the plasmonic microarray biochip 103, surface enhanced elastic scattering is produced during localized surface plasmon resonance, and the LSPR phase is amplified. Meanwhile, the localized temperature in vicinity of the titanium nitride nanocubes is increased through the photothermal excitation assembly 104, the specificity of target-receptor interaction is enhanced. The laser speckle image subjected to double enhancements is acquired by the optical interference assembly, the telecentric lens 105 and the imaging chip 106, and a more accurate phase is analyzed by using the sensitivity of a laser speckle to a localized refractive index change.

Figure 3:
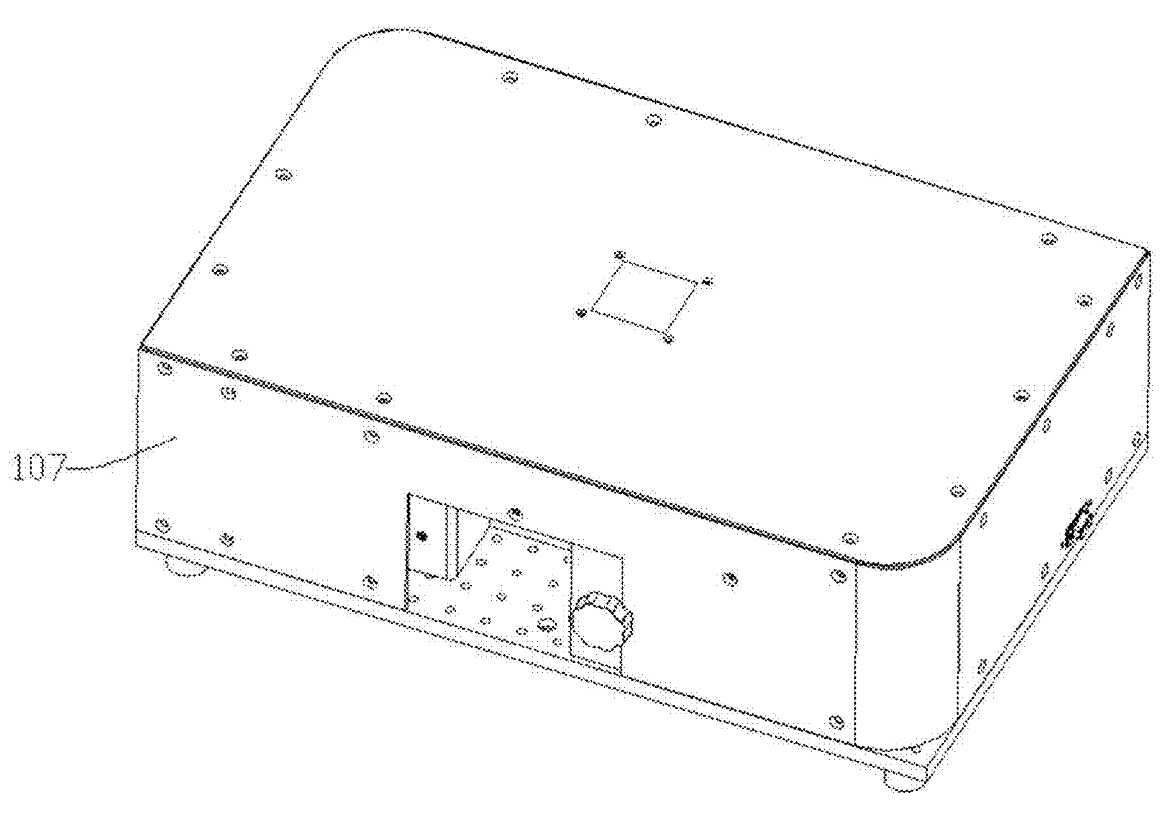
FIG. 3 is an outline drawing of the localized surface plasmon resonance biosensing device according to an embodiment of the disclosure.

Since the laser beam is sensitive to air turbulence in free convection, as shown in FIG. 3, the assemblies above are all mounted in a matt-black anodized aluminum enclosure 107, and separated from ambient airflow in biosensing measurement, thus improving the system stability.

As shown in FIG. 1 and FIG. 2, in some embodiments of the disclosure, a collimating unit 108 is arranged between the laser source 101 and the first linear polarizer 102.

Specifically, in some embodiments of the disclosure, the collimating unit 108 is a plano-convex lens, an output end of the laser source 101 is connected with a single mode fiber 109 of 3.5-micron core diameter, and an exit of the single mode fiber is positioned at a focus of the plano-convex lens, so that the laser is collimated to a Gaussian beam for probing.

Figure 4A:
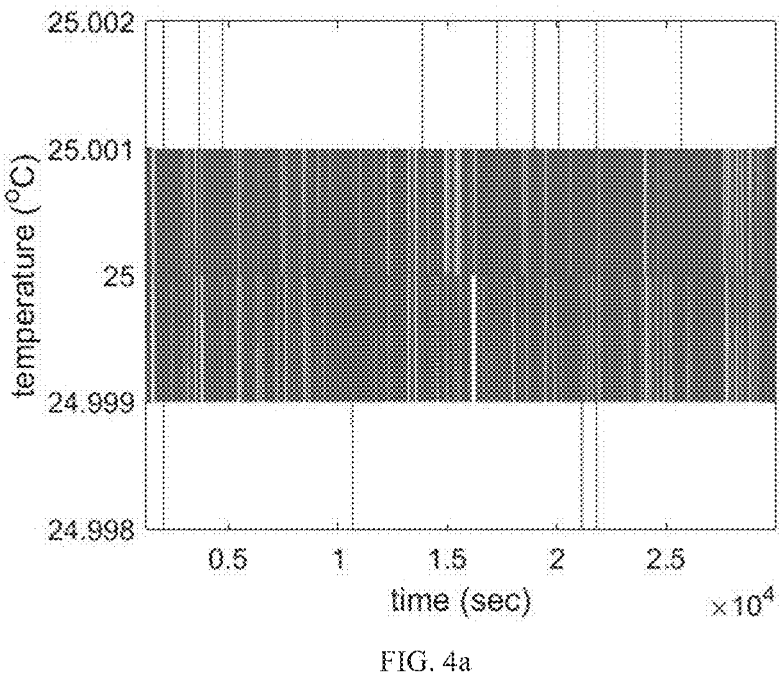
FIG. 4*a* and FIG. 4*b* are respectively a temperature oscillogram and a temperature variation distribution diagram of a single mode laser diode recorded in a period of 8 hours.
Figure 4B:
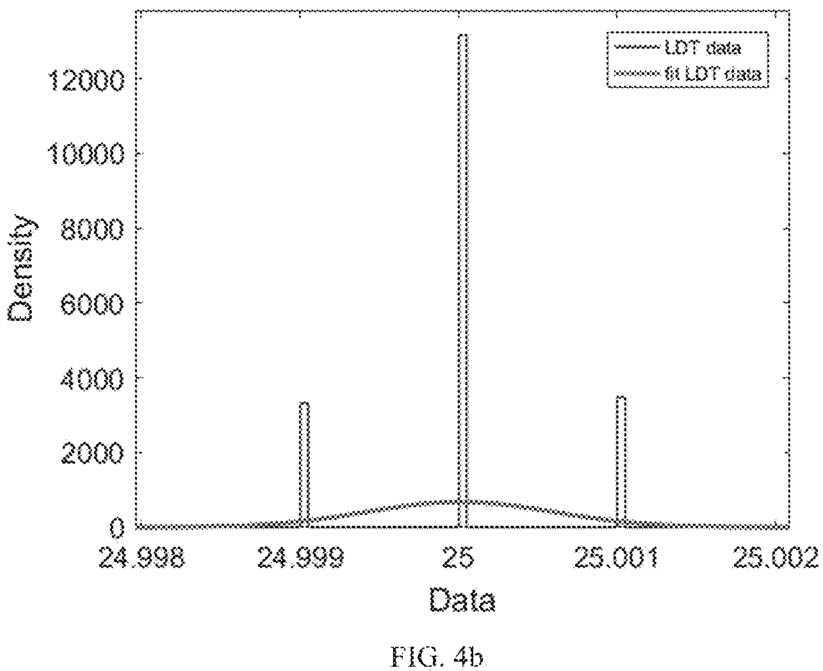

In addition, in some embodiments of the disclosure, the laser source 101 is a 640-nm single mode laser diode, with an optical power of 180 mW, a shell of the 640-nm single mode laser diode is connected with a first temperature sensor and a first thermoelectric cooler, and the first temperature sensor and the first thermoelectric cooler are electrically connected with a first temperature controller 110 respectively. The first temperature sensor detects a temperature signal of the 640-nm single mode laser diode in real time, and feeds the temperature signal back to the first temperature controller. The first temperature controller controls a temperature of the 640-nm single mode laser diode by adjusting an output power of the first thermoelectric cooler, and the temperature is stabilized at 25° C.±0.001° C. FIG. 4*a* and FIG. 4*b* are respectively a temperature oscillogram and a temperature variation distribution diagram of the single mode laser diode recorded in a period of 8 hours, and stable temperature control is convenient for keeping the consistent light intensity of the laser output.

In some embodiments of the disclosure, the photothermal excitation assembly 104 is a light emitting diode. As shown in FIG. 1, two light emitting diodes are provided in this embodiment, emitting at 590 nm with full-width-at-half-maximum (FWHM) of 20 nm and total optical output of about 1.2 W. The two light emitting diodes are respectively irradiated from two directions on the plasmonic microarray biochip 103 to induce the thermoplasmonic effect, which has the advantages as follows compared with irradiation by directly using a laser emitter: sizes and agglomeration of the titanium nitride nanocubes can affect the absorption wavelength of the photothermal effect, and there may be deviation from the optimal photothermal absorption wavelength if laser with a single wavelength is used, but the light emitting diodes has a wide the radiation waveband, thus having a good tolerance to titanium nitride and dye excitation. It can be understood that the photothermal excitation assembly 104 may also be replaced by other existing wide-waveband light sources.

As shown in FIG. 1 and FIG. 2, in some embodiments of the disclosure, the optical interference assembly comprises a light splitting prism 111, a first reflector 112 and a second reflector 113, the light splitting prism 111, the first reflector 112 and the second reflector 113 constitute a Michelson interferometer, a light incident surface of the light splitting prism 111 faces the plasmonic microarray biochip 103, and the first reflector 112 and the second reflector 113 are respectively located at a first interference port and a second interference port of the light splitting prism 111. The light splitting prism 111 is provided with a 50:50 beam splitter, and one half of the beam splitter is configured for reflection and the other half of the beam splitter is configured for transmission, which is realized by using an anti-reflection coating for a wavelength of 640 nm. A surface flatness of the first reflector 112 and the second reflector 113 is 1/10 of an incident wavelength. It should be pointed out that the Michelson interferometer is only used as one embodiment of the optical interference assembly, and other existing optical interference assemblies capable of achieving the same function are also suitable for the technical solution.

In some embodiments of the disclosure, the first reflector 112 is arranged on a kinetic mount configured for manually and finely adjusting a distance, so its position is finely adjusted then locked to achieve mechanical stability. The second reflector 113 is arranged on a piezoelectric ceramic phase shifter 114, the piezoelectric ceramic phase shifter 114 (PZT) is controlled by a high-voltage power amplifier driven by a 16 bits digital-to-analog converter (DAC), the total travel range of the PZT piezoelectric ceramic phase shifter 114 is 5 micrometers, and the total optical path difference is double to 10 micrometers as light travels back and forth in the Michelson interferometer. The theoretical resolution of the PZT driven by the 16 bits DAC is 10,000/65,536 that is about 0.15 nm. As the probe wavelength is 638 nm, the radian resolution is calculated by 0.15/640 which is about $1.5\times10^{-3}$ radian.

In some embodiments of the disclosure, a second linear polarizer 115 is arranged between the optical interference assembly and the telecentric lens 105, and the second linear polarizer 115 has a polarization direction rotated by 90 degrees relative to a polarization direction of the first linear polarizer 102. This is done to account for the extra phase retardation induced by the birefringence of PMMA polymer, of which the transparent substrate and the optical waveguide array of the plasmonic microarray biochip 103 are made, on 3D printing. Implementing the crossed polarizer pair helps to enhance the interference contrast.

Further, in some embodiments of the disclosure, a narrow-pass laser filter 116 is arranged between the telecentric lens 105 and the second linear polarizer 115. The narrow-pass laser filter 116 is a 10-nm FWHM bandpass filter centered at 640 nm, which can block a non-probing beam from entering the camera.

Figure 5A:
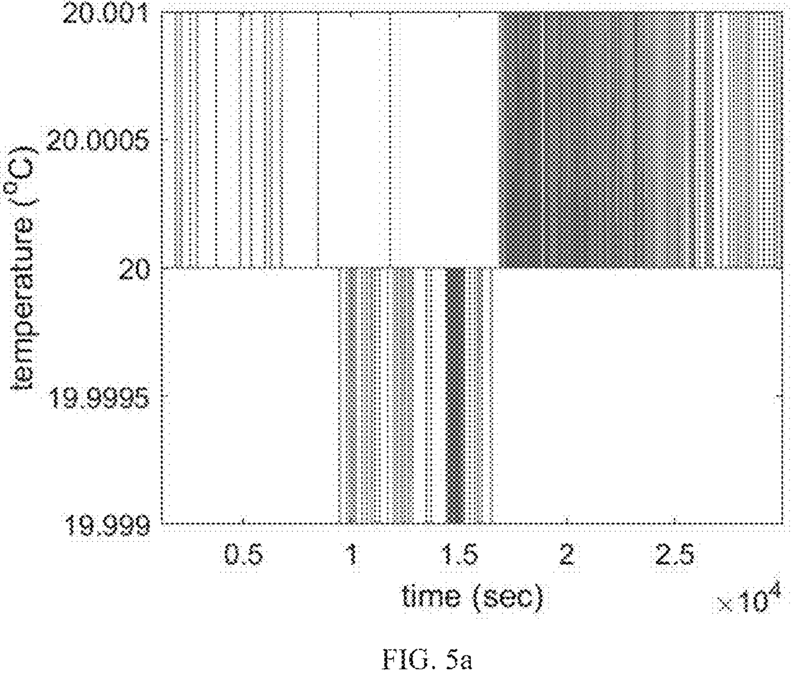
FIG. 5*a* and FIG. 5*b* are respectively a temperature oscillogram and a temperature variation distribution diagram of a CMOS imaging chip recorded in a period of 8 hours.
Figure 5B:
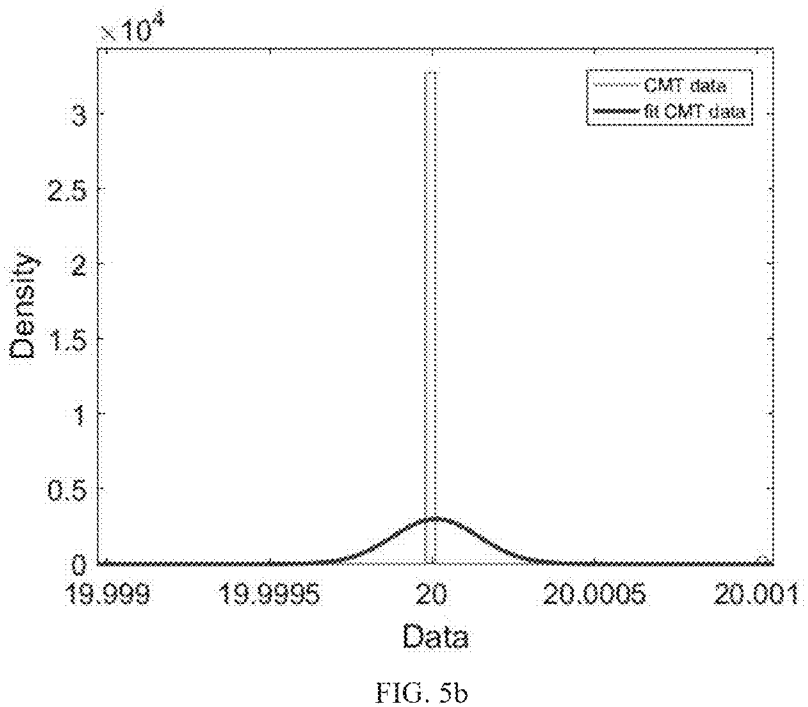

As shown in FIG. 1, in some embodiments of the disclosure, a shell of the imaging chip 106 is connected with a second temperature sensor and a second thermoelectric cooler, and the second temperature sensor and the second thermoelectric cooler are electrically connected with a second temperature controller 117 respectively. The second temperature sensor detects a temperature signal of the CMOS imaging chip 106 in real time, and feeds the temperature signal back to the second temperature controller 117. The second temperature controller 117 controls a temperature of the CMOS imaging chip 106 by adjusting an output power of the second thermoelectric cooler, and the temperature is stabilized to 20° C. with a standard deviation less than 0.001° C. for a period of 8 hours. FIG. 5*a* and FIG. 5*b* are respectively a temperature oscillogram and a temperature variation distribution diagram of the CMOS imaging chip 106 recorded in a period of 8 hours. It is important to state that the temperature of the CMOS imaging chip increases rapidly in operation and we found the maximum temperature difference attains 10° C. with room temperature of 25° C. Such temperature increment induces thermomechanical deflection of the CMOS chip, and as our theoretical resolution is in this range, the CMOS chip has to be thermally stabilized to attain the best stability. The CMOS chip records the elastic scattering of titanium nitride nanoparticles decorated on the PMMA waveguide on illumination by the probe laser beam. The elastically scattered laser produces laser speckles on the image plane of the imaging chip 106 and digitized by the CMOS camera after it passes through the optical interference assembly and the telecentric lens 105. Since we are measuring the phase change of plasmonic enhanced elastic scattering by TiNC, the measurement is entirely different from the attenuated total reflection as observed by conventional SPRi biosensor with thin metallic gold film. By FDTD calculation, it showed that the titanium nitride nanocubes in the presence of protein shell and dipoles could produce an obvious surface enhanced elastic scattering (SEES) effect.

In addition, in the technical solution, a phase direct-current power supply 118 and a MCU singlechip 119 are further provided. The phase direct-current power supply 118 provides operating voltages for the first temperature controller 110 and the second temperature controller 117 respectively. The MCU singlechip 119 is configured for analyzing a laser speckle signal of the CMOS imaging chip 106 on one hand, wherein the MCU singlechip 119 analyzes a phase of the laser speckle image in real time by using a phase-shifting algorithm, and is also configured for controlling operation of the piezoelectric ceramic phase shifter 114 (PZT) on the other hand.

The following description is a part of testing process and discovery of the technical solution, and before testing, it is necessary to transport a solution to be tested to a microfluidic channel on the plasmonic microarray biochip 103 through a peristaltic pump.

Figure 6:
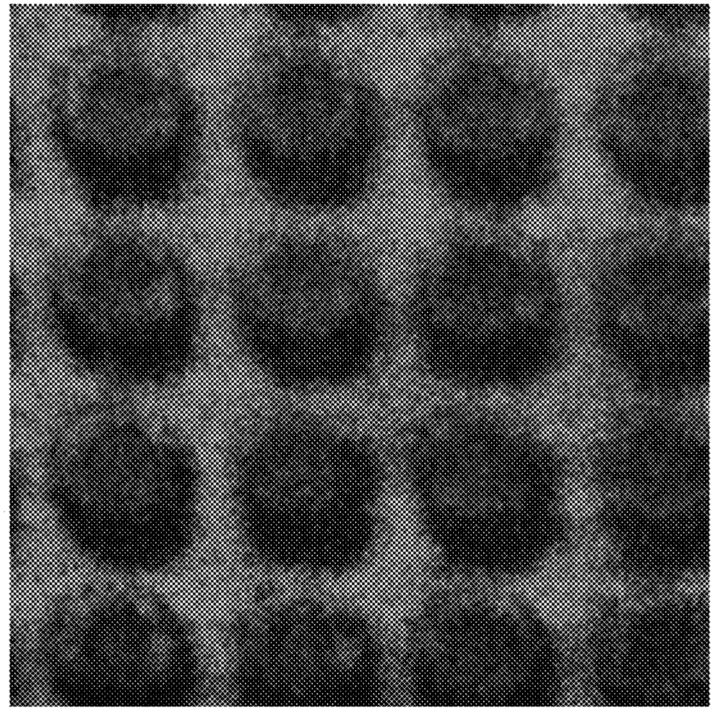
FIG. 6 is a raw intensity map of 700*700 pixels in a region-of-interest converted into gray scale.

FIG. 6 is a raw intensity map of 700*700 pixels converted into gray scale in a region-of-interest on the plasmonic microarray biochip 103. The region-of-interest (ROI) is 3 square millimeters, the optical waveguide is located at the center of each circle with a diameter of 500 um, and there are a total of 4*4 optical waveguides in the ROI on the plasmonic microarray biochip 103.

Figure 7:
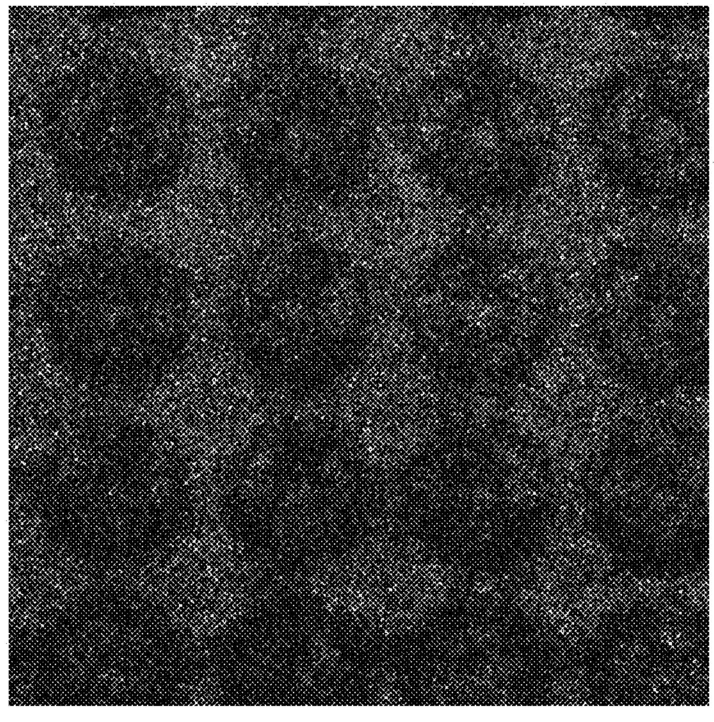
FIG. 7 is a phase map of 700*700 pixels in a region-of-interest filled with distilled water converted into gray scale.

The phase map of the ROI when the biochip 103 is filled with distilled water is shown in FIG. 7.

Figure 8:
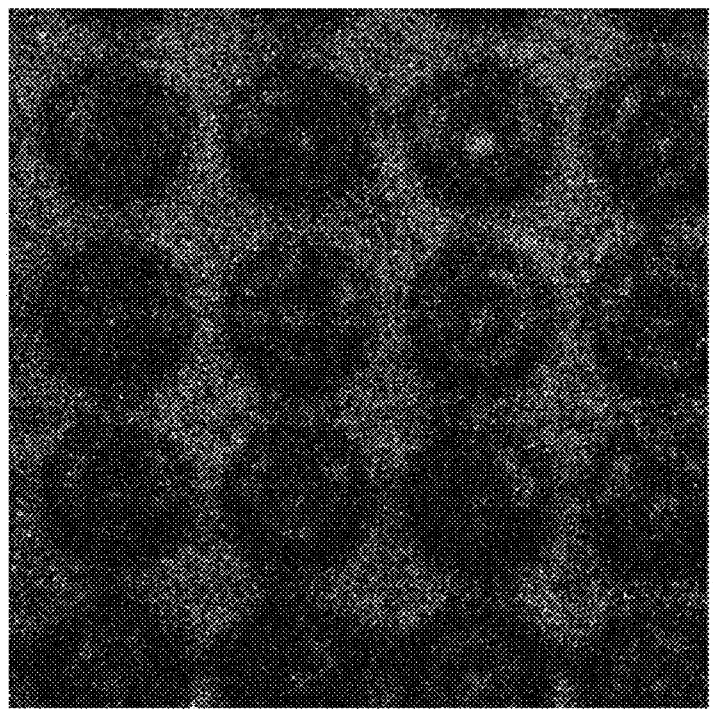
FIG. 8 is a phase map of 700*700 pixels in a region-of-interest filled with 1% sodium chloride solution converted into gray scale.

The phase map of the ROI when the biochip 103 is filled with 1% sodium chloride (NaCl) solution is shown in FIG. 8.

Figure 9:
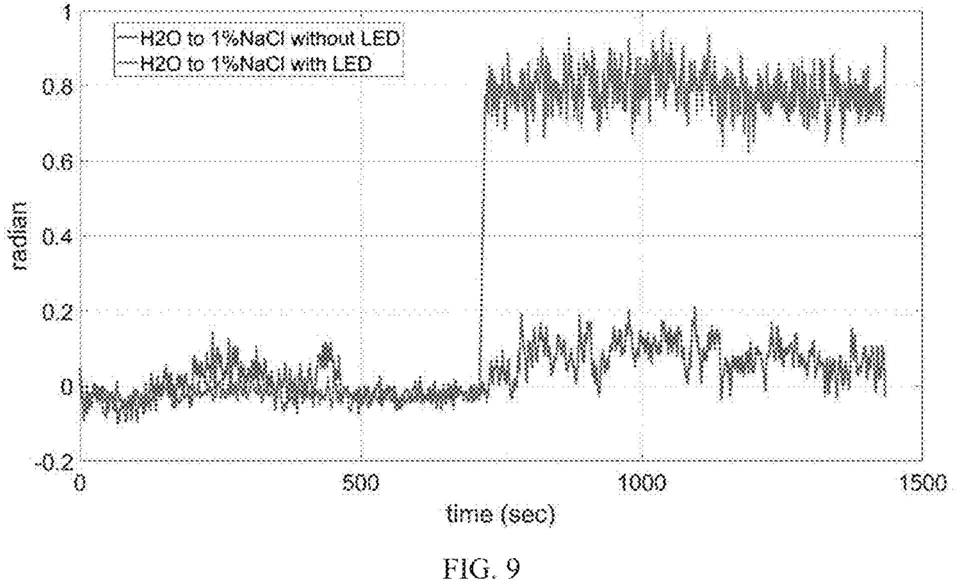
FIG. 9 is the selected pixel history as the refractive index changes from distilled water to 1% NaCl solutions with and without LED optical pumping.

In order to further demonstrate amplification of the photothermal excitation assembly 104 (pump-probe), the 1% NaCl solution is injected into the microfluidic channel of the biochip 103, and two 590-nm high-power LED emitters are switched on to generate photothermal amplification. The selected pixel history with and without LED optical pumping is shown in FIG. 9. By calculation, the maximum phase change due to 1% NaCl solution is 0.78 radian. Since the refractive index of the 1% NaCl solution at 20° C. is about $n=1.33172+1.4\times10^{-3}\times1$, which is 1.33312, and the refractive index of the distilled water at 20° C. is about 1.33300, the refractive index change is $1.2\times10^{-4}$ refractive index units (RIU). As the maximum phase change measured is 0.78 radians, the theoretical phase resolution is $1.5\times10^{-3}$ radians. The theoretical refractive index resolution (RIR) of our localized surface plasmon resonance biosensing device is estimated to $1.9\times10^{-7}$ RIU which is as good as conventional SPRi imaging biosensors.

Figure 10:
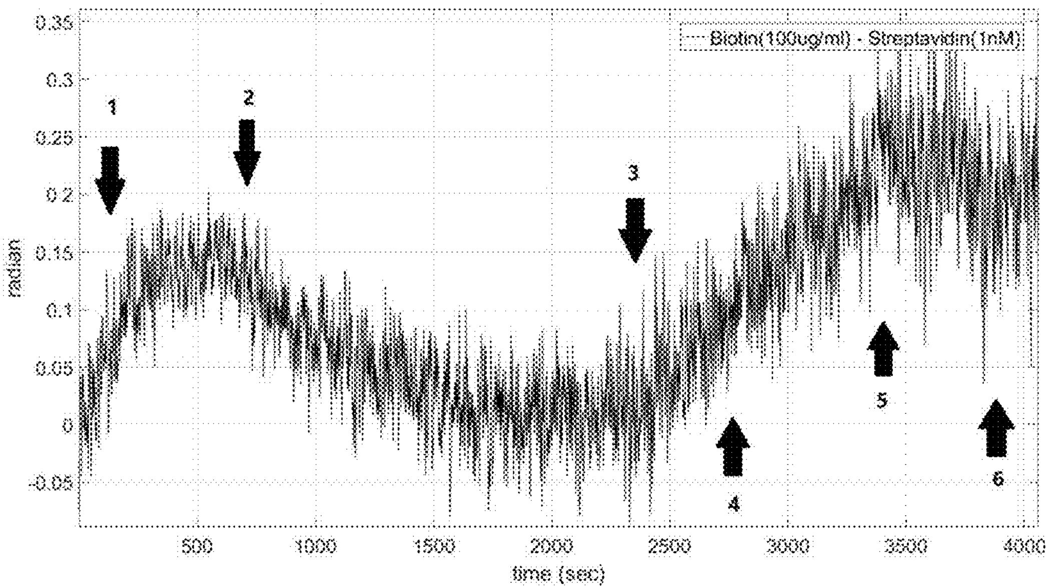
FIG. 10 is the selected pixel phase record as Biotin (100 ug/mL)—Streptavidin (1 nM) biochemical reaction is monitored with the optical waveguide array.
Figure 11:
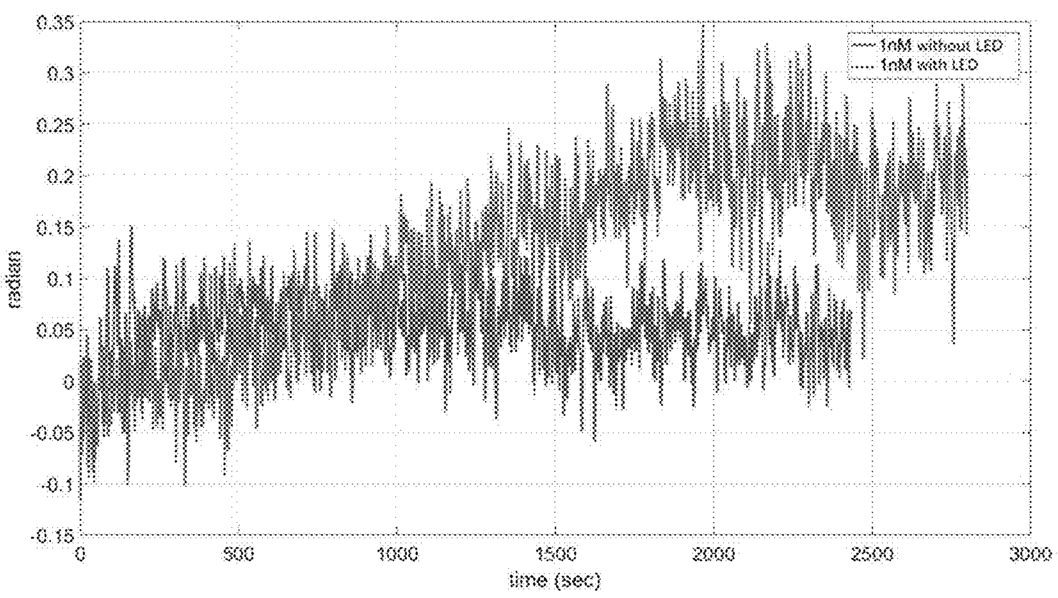
FIG. 11 is the selected pixel history record as Biotin-Streptavidin biochemical (100 ug/mL Biotin and 1 nM Streptavidin) reactions are monitored with and without optical pumping.

For biosensing application, we demonstrate the performance with biotin-streptavidin interaction. The biotin-streptavidin interaction is known as one of the strongest non-covalent interactions in nature. It is the ideal candidate to verify the biosensing performance of our novel biosensor. Besides, biotin is known to have high affinity towards the titanium nitride 200 (TiN200) surface by titanium-oxygen bonding. Therefore, it is expected that our localized surface plasmon resonance biosensing device shall reproduce biotin-streptavidin binding kinetics by measurement. The history of a selected pixel in the ROI is shown in FIG. 10, in which Biotin (100 ug/mL) —Streptavidin (1 nM) biochemical reaction is monitored with the optical waveguide array. At first, phosphate-buffered saline (PBS) was injected into the biochip 103 at flow rate of 10 ul/min (data not shown). Then biotin solution of 100 ug/ml in PBS buffer was injected into the biochip 103 at the same rate (as indicated by arrow 1). After 8 minutes, PBS buffer was injected at the same flow rate again to flush away any biotin molecules not absorbed (as indicated by arrow 2). Then, 1 nM streptavidin in PBS buffer was flow into the biotin functionalized biochip 103 at the same rate (as indicated by arrow 3). After 4 minutes, the peristaltic pump was stopped, and the two LEDs are switched fully on (as indicated by arrow 4), and streptavidin was allowed to react with biotin on the titanium nitride nanocubes. After 12 minutes, the LEDs are switched off (as indicated by arrow 5). The phase change is measured by the localized surface plasmon resonance biosensing device with and without LED amplification as shown in FIG. 11. As 1 nM Streptavidin produced about 0.25 radian change with LED pumping, provided that the phase resolution of the localized surface plasmon resonance biosensing device is $1.5\times10^{-3}$ radians, the theoretical limit of detection for biotin-Streptavidin with the localized surface plasmon resonance biosensing device is estimated to 6 pM which is better than the specification of existing 32 channels SPRi biosensor with detection limit of 10 pM.

With the above experimental results, we are convinced that laser speckle imaging with phase measurement by optical interferometry is an effective way for label-free LSPR biosensing.

Figure 12:
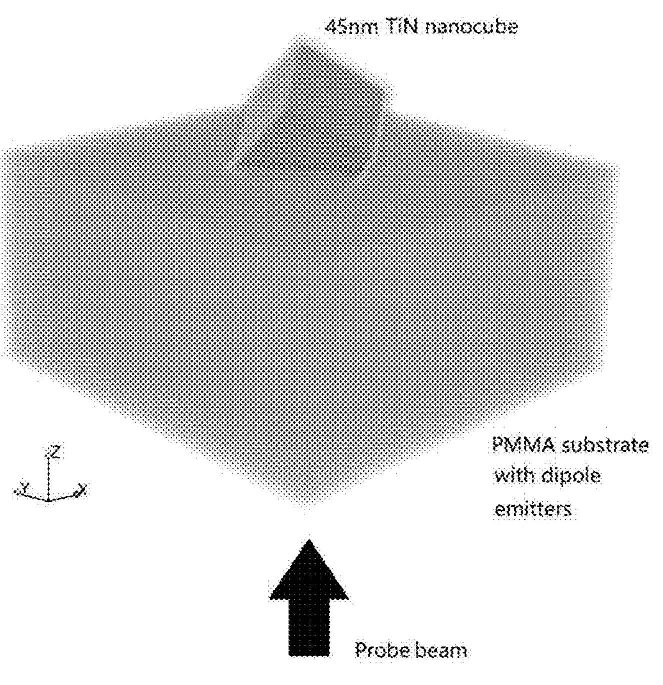
FIG. 12 is the geometric model of a 45-nanometer titanium nitride nanocube (TiNC) partially embedded in PMMA substrate for FDTD computation.

In order to further understand the origin of laser speckles produced by LSPR of TiNC, FIG. 12 shows a model of the titanium nitride nanocube in this embodiment, which consists of a single TiN nanocube of size 45 nm partially embedded in the PMMA substrate. The refractive index above the TiN nanocube is defined as water which is 1.3330. The probe laser beam is polarized in the y direction. The entire model occurs 0.8×0.8×0.8 micron (e.g., 800 nm in XYZ directions) with spatial resolution of 2 nm and the simulation runtime is configured to be 100 periods of the incident wavelength of 638 nm. This is done to ensure that sufficient cycles are collected by the discrete Fourier transform (DFT) monitor for field data processing. Near-to-far field conversion is computed based on the following steps, (1) a near surface is defined as monitor to capturing outgoing radiation in the desired direction, (2) the simulation is run using a pulsed source to allow MEEP package to accumulate the DFT fields on the monitor, (3) the far field scattering intensity and phase at any desired points is computed by the MEEP package.

Figure 13:
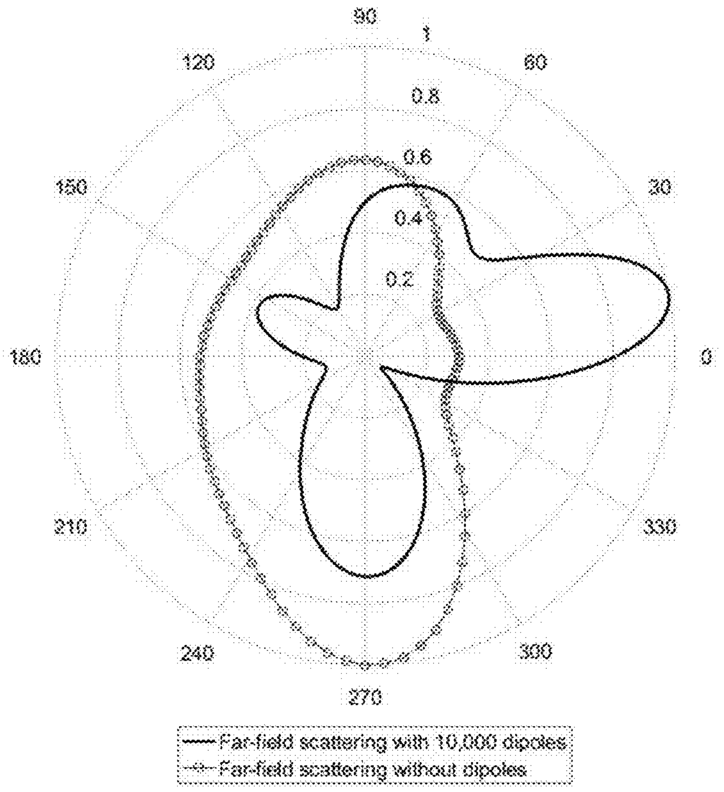
FIG. 13 is the far field scattering pattern of the 45-nanometer titanium nitride nanocube (TiNC) and the far field scattering pattern of the same 45-nanometer TiNC.

Far field scattering intensity of the 45 nm TiNC at a distance of 0.45 mm is shown in FIG. 13 as the thin curve with circular mark. The wavefront of the 640 nm incident wave is distorted due to the presence of the TiNC. The Poynting vector in the direction of 60 degrees and 120 degrees are smaller than that at 90 degrees in the Z direction vertical to the XY plane. So, intensity fluctuation is expected as the directional energy flux per area differs. This is the root cause of laser speckles observed in experiment as shown in FIG. 6.

In order to more clearly know how biochemical interaction on the TiNC changes the laser speckle, in this embodiment, material above the nanocube geometry was deliberately changed to protein (n=1.5500) and recalculated the far field scattering intensity at the same distance as shown in the solid curve in FIG. 13. Dipoles of 10,000 in number was placed in close proximity to the TiNC. It is obvious that the far field scattering pattern of TiNC in the presence of protein shell and dipoles is much different from the previous case. For the measurement in vertical direction near 90 degrees, the Poynting vector intensity changed from 0.65 to 0.50, reduced by over 20%. This is a significant change to the recorded intensity, so does the change to optical phase measurement. Therefore, by FDTD calculation, the elastic scattering at incident wavelength of 640 nm is enhanced by the presence of the near-field dipole pumping to the 45 nm TiNC.

Thus, it can be concluded that:

(1) the far-field laser speckles observed are due to the surface enhanced elastic scattering (SEES) by localized surface plasmon resonance of the TiNC structure; and (2) the far-field laser speckles are sensitive to the refractive index change occurred on the nano-surface, so accompanied laser speckle phase change is effective in measuring near-field biochemical reaction happened on the titanium nitride nanocube by near-field dipole pumping.

It is also important to state that there is a plurality of TiNCs on the biochip, so the observed scattering is the combination of multiple TiNCs. So, the initial phase of every camera pixel is random and laser speckle is observed and the pixel-wise phase value can only be retrieved by algorithm from multiple frames.

The embodiments of the disclosure are described in detail with reference to the drawings above, but the disclosure is not limited to the above embodiments, and various changes may also be made within the knowledge scope of those of ordinary skills in the art without departing from the purpose of the disclosure.

The invention claimed is:

1. A localized surface plasmon resonance biosensing device, comprising:

a laser source configured for outputting probe laser;

a first linear polarizer arranged in front of the laser source and configured for linearly polarizing the probe laser;

a plasmonic microarray biochip arranged in front of the first linear polarizer to receive the linearly polarized probe laser, wherein the plasmonic microarray biochip comprises a transparent substrate, and an optical waveguide array made of a PMMA polymer and a microfluidic channel, which are arranged at a middle portion of the transparent substrate, and an optical waveguide side surface of the optical waveguide array is provided with titanium nitride nanocubes, a photothermal excitation assembly configured for outputting an optical wave acted on the optical waveguide array of the plasmonic microarray biochip;

an optical interference assembly arranged in a transmitted light path of the plasmonic microarray biochip and configured for converting laser transmitted by the plasmonic microarray biochip into double beams meeting an interference condition;

a telecentric lens arranged on an output side of the optical interference assembly and configured for focusing the double beams; and an imaging chip arranged at a tail portion of the telecentric lens and configured for acquiring a laser speckle image formed by interference of the double beams;

wherein a second linear polarizer is arranged between the optical interference assembly and the telecentric lens, and the second linear polarizer has a polarization direction rotated by 90 degrees relative to a polarization direction of the first linear polarizer to compensate a phase retardation induced by the PMMA polymer;

wherein the optical interference assembly comprises a light splitting prism, a first reflector and a second reflector, a light incident surface of the light splitting prism faces the plasmonic microarray biochip, and the first reflector and the second reflector are respectively located at a first interference port and a second interference port of the light splitting prism;

wherein the first reflector is arranged on a kinetic mount capable of manually and finely adjusting a distance, and the second reflector is arranged on a piezoelectric ceramic phase shifter.

2. The localized surface plasmon resonance biosensing device of claim 1, wherein a collimating unit is arranged between the laser source and the first linear polarizer.

3. The localized surface plasmon resonance biosensing device of claim 2, wherein the collimating unit is a plano-convex lens, an output end of the laser source is connected with a single mode fiber, and an exit of the single mode fiber is located at a focus of the plano-convex lens.

4. The localized surface plasmon resonance biosensing device of claim 1, wherein the laser source is a 640-nm single mode laser diode, a shell of the 640-nm single mode laser diode is connected with a first temperature sensor and a first thermoelectric cooler, and the first temperature sensor and the first thermoelectric cooler are electrically connected with a first temperature controller respectively.

5. The localized surface plasmon resonance biosensing device of claim 1, wherein the photothermal excitation assembly is a light emitting diode.

6. The localized surface plasmon resonance biosensing device of claim 1, wherein a narrow-pass laser filter is arranged between the telecentric lens and the second linear polarizer.

7. The localized surface plasmon resonance biosensing device of claim 1, wherein a shell of the imaging chip is connected with a second temperature sensor and a second thermoelectric cooler, and the second temperature sensor and the second thermoelectric cooler are electrically connected with a second temperature controller respectively.

* * * * *